(12) United States Patent
Mandala et al.

(10) Patent No.: US 10,815,223 B2
(45) Date of Patent: Oct. 27, 2020

(54) PROCESS FOR PRODUCING LAMIVUDINE AND EMTRICITABINE

(71) Applicant: Nelson Mandela Metropolitan University, Port Elizabeth (ZA)

(72) Inventors: Devender Mandala, Hanamkonda-Telangana (IN); Paul Watts, Port Elizabeth (ZA)

(73) Assignee: Nelson Mandela Metropolitan University, Port Elizabeth (ZA)

( * ) Notice: Subject to any disclaimer, the term of this patent is extended or adjusted under 35 U.S.C. 154(b) by 0 days.

(21) Appl. No.: 16/301,255

(22) PCT Filed: Jun. 13, 2017

(86) PCT No.: PCT/IB2017/053481
§ 371 (c)(1),
(2) Date: Nov. 13, 2018

(87) PCT Pub. No.: WO2017/216709
PCT Pub. Date: Dec. 21, 2017

(65) Prior Publication Data
US 2019/0211004 A1    Jul. 11, 2019

(30) Foreign Application Priority Data
Jun. 14, 2016   (GB) .................................. 1610327.7

(51) Int. Cl.
*C07D 411/04*   (2006.01)

(52) U.S. Cl.
CPC ........ *C07D 411/04* (2013.01); *C07B 2200/13* (2013.01)

(58) Field of Classification Search
CPC .................................................. C07D 411/04
USPC ........................................................ 544/317
See application file for complete search history.

(56) References Cited

U.S. PATENT DOCUMENTS

| | | | | |
|---|---|---|---|---|
| 5,210,085 A * | 5/1993 | Liotta | ................. | C07D 327/04 514/274 |
| 5,248,776 A * | 9/1993 | Chu | .................... | A61K 31/675 544/180 |
| 6,346,627 B1 * | 2/2002 | Liotta | ................. | C07D 327/04 549/29 |
| 2003/0013880 A1 * | 1/2003 | Murthy | ............... | C07D 411/04 544/317 |
| 2010/0063283 A1 * | 3/2010 | Li | ....................... | C07D 327/04 544/317 |
| 2011/0039798 A1 * | 2/2011 | Doncel | ................ | C07H 19/06 514/46 |

FOREIGN PATENT DOCUMENTS

| | | | | |
|---|---|---|---|---|
| CN | 103951561 A | * | 7/2014 | |
| WO | WO-2011107920 A1 | * | 9/2011 | ........... C07D 411/04 |
| WO | 2013021290 | | 2/2013 | |
| WO | WO-2013021290 A1 | * | 2/2013 | ........... C07D 411/04 |

OTHER PUBLICATIONS

CAS Abstract CN 103951561 (2014) (Year: 2014).*
F. Fernandez et al., 20 Synthetic Communications, 2837-2847 (1990) (Year: 1990).*
English Language Machine Translation of CN 103951561 (2014) (Year: 2014).*
M. Baumann et al., Beilstein Journal of Organic Chemistry, 1194-1219 (2015) (Year: 2015).*
M.D. Goodyear et al., 46 Tetrahedron Letters, 8535-8538 (2005) (Year: 2005).*
J. Mann et al., Journal of the Chemical Society, Perkin Transactions 1: Organic and Bio-Organic Chemistry, 3141-3148 (1994) ( Year: 1994).*
Mandala, Devender, et al., "Semi-Continuous Multi-Step Synthesis of Lamivudine", Organic & Biomolecular Chemistry, Mar. 27, 2017, vol. 15, No. 6, pp. 3444-3454.
International Search Report based on co-pending International Application No. PCT/IB2017/053481, dated Jan. 15, 2018, 3 Pages.
Written Opinion based on co-pending International Application No. PCT/IB2017/053481, dated Jan. 15, 2018, 5 Pages.

* cited by examiner

*Primary Examiner* — Mark L Shibuya
*Assistant Examiner* — Ebenezer O Sackey
(74) *Attorney, Agent, or Firm* — McCarter & English, LLP (57) ABSTRACT

This invention provides for flow and batch synthesis processes for the production of Lamivudine and Emtricitabine, including flow and batch synthesis processes wherein at least of the synthesis steps are conducted in a solvent free environment.

12 Claims, 2 Drawing Sheets

PROCESS FOR PRODUCING LAMIVUDINE AND EMTRICITABINE

CROSS-REFERENCE TO RELATED APPLICATIONS

This application is a national stage application filed under 35 U.S.C. § 371 of PCT/IB2017/053481, filed Jun. 13, 2017, which claims the benefit of Great Britain Patent Application No. 1610327.7, filed Jun. 14, 2016, each of which is incorporated herein, in its entirety, by reference.

INTRODUCTION

This invention relates to a process for producing Lamivudine and Emtricitabine, in particular, but not exclusively, to a process for producing Lamivudine and Emtricitabine wherein at least one of the steps of the process is solvent free, and wherein the process is a semi-continuous or fully continuous flow synthesis process.

BACKGROUND

Emtricitabine and Lamivudine are used as antivirals drugs. Emtricitabine differs from Lamivudine in that it comprises a fluorine atom in the 5-position.

There are numerous processes and synthetic routes described in the prior art for the preparation of Emtricitabine and Lamivudine.

However, existing synthesis methodologies for the production of these compounds have essentially been based on standard stirred batch reactor type processes, wherein significant volumes of organic solvents are used. In addition, these processes typically isolate process intermediates at each step of the process, thereby further increasing the usage of solvents. The relatively high cost of APIs produced in this manner is therefore largely based on this reliance on organic solvents, and the inherent process inefficiencies leading from the isolation of intermediates.

Micro reactor technology (MRT), more recently branded 'flow chemistry', is an emerging technique that enables those working in research and development to rapidly screen reactions utilising continuous flow, leading to the identification of reaction conditions that are suitable for use at a production level. Furthermore, in addition to using conventional reaction methodology, the inherent safety associated with the use of small reactor volumes enables users to employ reaction conditions previously thought to be too hazardous for use within a production environment; such as extreme reaction conditions or the use/generation of 'hazardous' compounds. Consequently, the type of reactions available to the chemist increases through the use of this technology.

To date there is no process for the production of Emtricitabine or Lamivudine based on flow chemistry, or a process wherein the need for organic solvents is eliminated in some of the steps of the process.

The present invention seeks to address some of the shortcomings of the prior art by providing new processes for the production of Emtricitabine or Lamivudine.

SUMMARY OF THE INVENTION

According to a first aspect to the present invention there is provided a flow synthesis process for producing a compound of the Formula I and its pharmaceutically acceptable salts, Formula I the process comprising the steps of:

a) reacting L-menthyl glyoxalate with 1,4-dithiane-2,5-diol in a dehydration reaction to form a reaction product comprising a compound of the Formula Ia

Formula Ia b) reacting the reaction product of step (a) with an appropriate acetylation reagent to form a reaction product comprising a compound of the Formula Ib Formula Ib c) reacting the reaction product of step (b) with a compound of the Formula Ic Formula Ic in a glycosylation reaction to from a reaction product comprising a compound of the Formula Id Formula Id and d) reacting the reaction product of step (c) with a reducing agent to form the compound of Formula I, wherein R is selected from H or F, and wherein steps (a) to (b) and (c) to (d) are continuous flow synthesis steps, such that the compound of Formula Ib is the only intermediate isolated in the process.

In a preferred embodiment steps (a) to (d) are continuous flow synthesis steps, such that no isolated intermediates are produced in the process.

In one embodiment, prior to step (a) the L-menthyl glyoxalate is produced from a reaction of L(−) menthol with glyoxalic acid in cyclohexane, wherein the L(−) menthol is recovered as a by-product from the reaction mixture formed in step (d).

Preferably, the compound of Formula Ic

Formula Ic used in step (c) is produced by reacting a compound of Formula II

Formula II with Bis(trimethylsilyl)acetamide in the presence of an organic solvent.

Preferably, the organic solvent is acetonitrile.

In a preferred embodiment, the reaction in step (a), step (b), or both steps (a) and (b) is a solvent-free reaction.

In another embodiment, in step (a) the reaction of L(−) Menthyl glyoxalate and 1,4-dithiane-2,5-diol is conducted in an organic solvent.

In one embodiment, in step (b) the acetylation reagent is a mixture of acetic anhydride and pyridine, or acetic anhydride and sodium carbonate.

In a further embodiment, in step (b) the acetylation reaction of the compound of Formula Ia Formula Ia is conducted in the presence of an organic solvent.

Preferably, the organic solvent in steps (a) and (b) is selected from the group consisting of acetone, dichloromethane, and mixtures thereof In one embodiment, in step (c) the compound of Formula Ic Formula Ic is reacted with the compound of Formula Ib Formula Ib and trimethylsilyl iodide or pyridine triflate n the presence of an organic solvent.

Preferably, the organic solvent of step (c) is acetonitrile.

According to a second aspect to the present invention there is provided a batch process for producing a compound of the Formula I and its pharmaceutically acceptable salts, Formula I the process comprising the steps of:

a) reacting L-Menthyl glyoxalate with 1,4-dithiane 2,5-diol to form a reaction product comprising a compound of the Formula Ia

Formula Ia b) reacting the compound of Formula Ia with an acetylation reagent, optionally in the presence of an organic solvent, to form a reaction product comprising a compound of the Formula Ib

Formula Ib c) reacting the compound of Formula Ib with a compound of the Formula Ic Formula Ic and iodotrimethylsilane in the presence of the organic solvent to from a reaction product comprising a compound of the Formula Id Formula Id and d) reacting the compound of Formula Id with a reducing agent to form the compound of Formula I,
wherein R is selected from H or F.

In a preferred embodiment, the acetylation reagent is a mixture of acetic anhydride and sodium carbonate.

In a preferred embodiment, the reaction in step (a), step (b), or both steps (a) and (b) is a solvent-free reaction.

In a preferred embodiment, the organic solvent in steps (b) and (c) is acetonitrile.

In one embodiment, in step (a) the compound of the Formula Ia

Formula Ia is crystallised from the reaction product with a mixture of trimethylamine and heptane.

In another embodiment, in step (b) the compound of the Formula Ib

Formula Ib is crystallised from the reaction product with a mixture of trimethylamine and hexane.

Preferably, in step (c) the reaction product is purified by column chromatography using a mobile phase of methanol and dichloromethane, after which the compound of the Formula Id Formula Id is recrystallised with a mixture of ethyl acetate, hexane, and methanol.

BRIEF DESCRIPTION OF THE DRAWINGS

The invention will now be described in more detail with reference to the following non-limiting embodiments and figures in which.

DETAILED DESCRIPTION OF A PREFERRED EMBODIMENT

Figure 1:
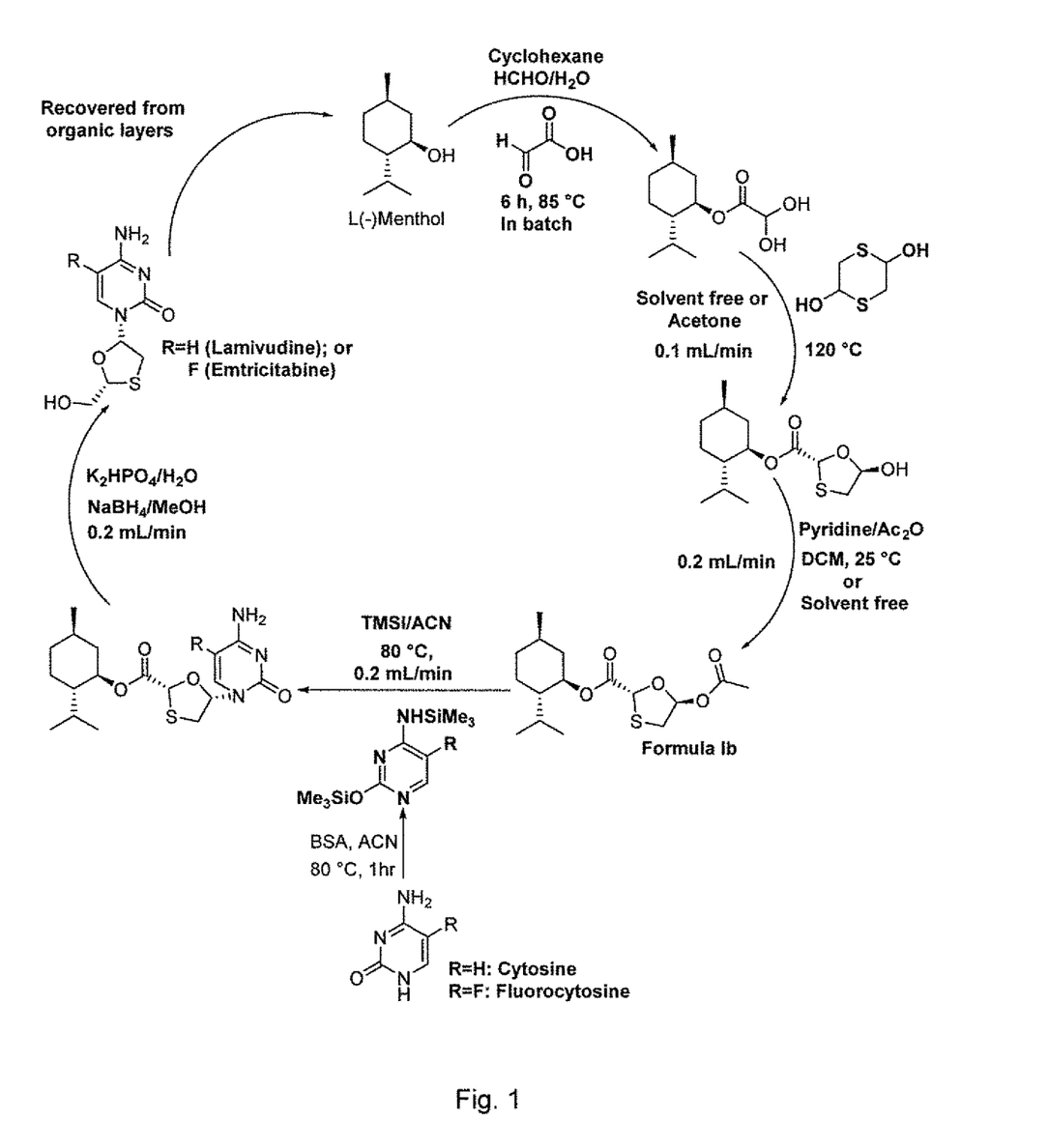
FIG. 1 shows a synthesis diagram for a semi-continuous flow synthesis process for producing Lamivudine and Emtricitabine.
Figure 2:
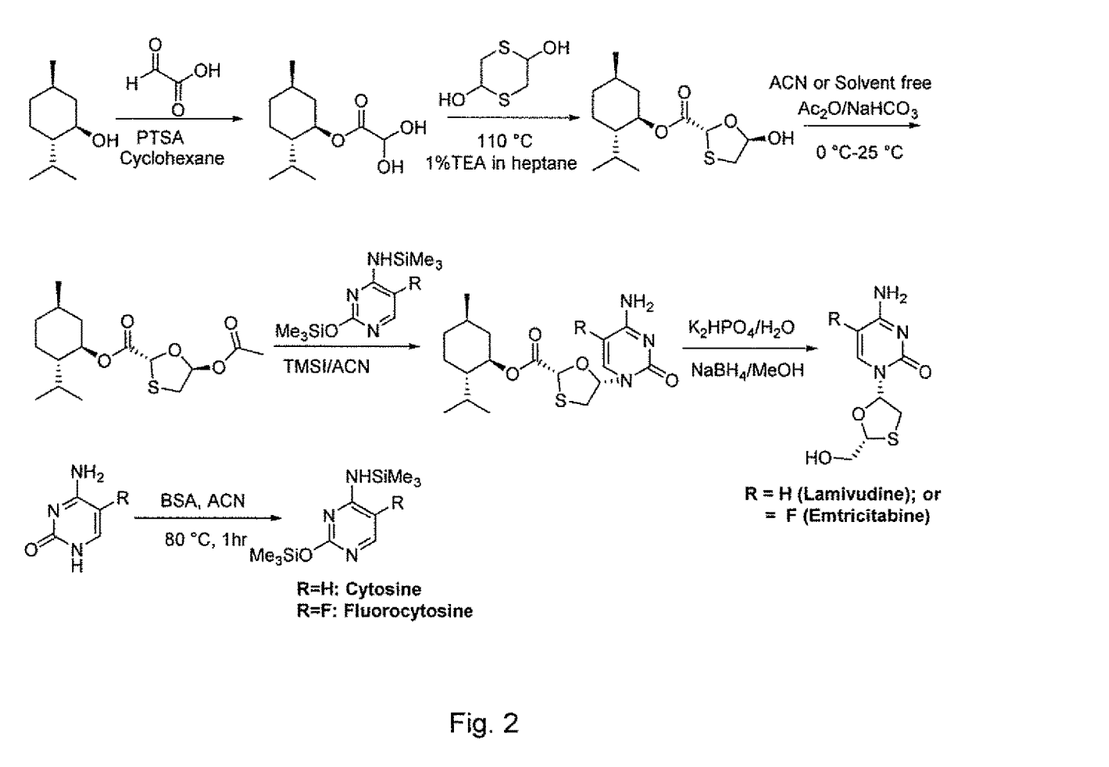
FIG. 2 shows a synthesis diagram for a batch synthesis process for producing Lamivudine and Emtricitabine.

The invention as described hereinafter should not be construed to be limited to the specific embodiments disclosed, with slight modifications and other embodiments intended to be included within the scope of the invention.

Although specific terms are employed herein, they are used in a generic and descriptive sense only and not for purposes of limitation.

As used herein, throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having", "including", and variations thereof used herein, are meant to encompass the items listed thereafter, and equivalents thereof as well as additional items.

The present invention provides for a process for producing Lamivudine and Emtricitabine, and its pharmaceutically acceptable salts, wherein Lamivudine and Emtricitabine are represented by Formula I having the following structure:

and wherein R is selected from H or F.

The present invention provides, in particular, for a process for producing Lamivudine and Emtricitabine with a process wherein at least one of the reactions of the process is conducted in the absence of a solvent. The process may be a batch process, a semi-continuous flow synthesis process, or a fully continuous flow synthesis process.

Where used in this specification the term "semi-continuous flow synthesis process" should be understood to mean a flow synthesis process comprising a number of steps, wherein a majority of the steps are continuous without the isolation of a process intermediate.

Where used in this specification the term "fully continuous flow synthesis process" should be understood to mean a flow synthesis process comprising a number of steps, wherein the final product of the process is obtained without the isolation of any process intermediate.

In both the batch and flow synthesis configurations of the process, the first reaction, or the first two reactions, of the process may be conducted in an environment that is solvent free. The first two reactions being 1) the formation of (2R,5R)-((1R,2S,5R)-2-isopropyl-5-methylcyclohexyl) 5-hydroxy-1,3-oxathiolane-2-carboxylate (Formula Ia) from the reaction of L(−) Menthyl glyoxalate with 1,4-dithiane 2,5-diol, and 2) the formation of (2R,5R)-((1R,2S,5R)-2-isopropyl-5-methylcyclohexyl) 5-acetoxy-1,3-oxathiolane-2-carboxylate (Formula Ib) from the reaction of the reaction product of the first reaction with acetic anhydride or acetic anhydride and sodium bicarbonate. It will be appreciated by those persons skilled in the art that while the solvent free reactions may be demonstrated in the batch configuration, that the processes may be transferred to the flow synthesis configuration with the appropriate instrumentation.

In the flow synthesis configuration of the process, the process may either be a semi-continuous flow synthesis process or a fully continuous flow synthesis process. In the semi-continuous flow synthesis process the first two steps of the reaction is conducted in an organic solvent after which (2R,5R)-((1R,2S,5R)-2-isopropyl-5-methylcyclohexyl) 5-acetoxy-1,3-oxathiolane-2-carboxylate (Formula Ib) is isolated as an intermediate, to be reconstituted for use in the further steps of the process. The intermediate may be isolated because the solvents used in the first stage of the process are not miscible with the solvents used in the later stage of the process, for example.

However, the process may also be operated in a fully continuous manner. In this flow synthesis process no intermediates are isolated. A fully continuous flow synthesis process may be achieved through the selection of reaction solvents that are miscible across the entire process, or alternatively by conducting some of the steps of the process in a solvent free environment. Both the semi-continuous and fully continuous flow synthesis processes, lead to a reduction in time and cost, partly as a result of reduced solvent use, compared to conventional synthesis process for Lamivudine and Emtricitabine.

In both the batch and flow synthesis configurations of the process, the L(−) Menthyl glyoxalate starting material may be prepared by the reaction of L(−) Menthol with glyoxalic acid according to the method as described in *Synthetic Commun.* 1990, 20, 2837-2847, the disclosure of which is incorporated herein by reference. The L(−) Menthol used in the production of L(−) Menthyl glyoxalate may be recovered from the organic layers produced in the step of preparing Lamivudine and Emtricitabine by the reduction of (2R,5R)-((1R,2S,5R)-2-isopropyl-5-methylcyclohexyl) 5-acetoxy-1,3-oxathiolane-2-carboxylate (Formula Id).

The L(−) Menthol may be recovered from the organic solvent used in the purification of the final product of the reduction reaction. After completion of final reaction with $NaBH_4$, the reaction mixture was quenched with dilute hydrochloric acid, adjusted the pH to 4-4.5 (the lamivudine and emtricitabine is present in the salt form in the aqueous layer), and washed with toluene and diethyl ether to recover the menthol, which was purified by further solvent washings.

In both the batch and flow synthesis configurations of the process, the silylated cytosine or fluorocytosine may be produced by the reaction of the particular cytosine starting compound with Bis(trimethylsilyl)acetamide in an organic solvent under inert atmosphere. In the flow synthesis configuration of the process the silylated cytosine or silylated fluorocytosine can be introduced into the flow synthesis process at a certain predetermined flow rate to react with (2R,5R)-((1R,2S,5R)-2-isopropyl-5-methylcyclohexyl) 5-acetoxy-1,3-oxathiolane-2-carboxylate (Formula Ib). The compound of Formula Ib may either by introduced as a reconstituted isolated intermediate (semi-continuous), or as a non-isolated component of the reaction product of the previous reactions (fully continuous).

The present invention will now be described more fully hereinafter with reference to some of the non-limiting embodiments of the invention.

General Experimental Procedures

All the batch reactions were performed in an oven dried glassware. Solvent and chemicals were obtained from Aldrich and Alfa Aesar Company. All other reagents and solvents were used as obtained without further purification. All the moisture-sensitive reactions were performed under nitrogen atmosphere using oven-dried glassware.

The syringe pump and stainless syringes (1 ml, 5 mL and 10 mL) were purchased from Supelco Company. PFA tubing refers to perfluoro alkoxy alkane tubing. PFA and Tygon MHLL tubing were purchased from IDEX Health & Sciences.

Analytical thin-layer chromatography (TLC) was performed using EMD silica gel 60 F254 plates. The products were visualized by UV light (254 nm), iodine vapor and/or the use of KMnO$_4$ stain.

$^1$H and $^{13}$C NMR spectra were recorded on a Bruker AvanceIII-400 spectrometer (400 and 100 MHz, respectively) in DMSO-d$_6$ and CDCl$_3$. Chemical shifts in $^1$H NMR spectra are reported in parts per million (ppm) on the ∂ scale from an internal standard of residual CHCl$_3$ in CDCl$_3$ (7.26 ppm), MeOH in MeOD (3.31 ppm) or DMSO in DMSO-d$_6$ (2.50 ppm). Data are reported as follows: chemical shift, multiplicity (s=singlet, d=doublet, t=triplet, q=quartet, quint=quintet, m=multiplet, and br=broad), coupling constant in hertz (Hz), and integration. Chemical shifts of $^{13}$C NMR spectra are reported in ppm from the central peak of CDCl$_3$ (77.16 ppm), MeOD (49.15 ppm) or DMSO-d$_6$ (39.52 ppm) on the ∂ scale. $^{13}$C signals with identical chemical shifts for more than one carbon are specified, and overlapping peaks for multiple carbons are indicated by a shift range. Infrared (IR) spectra were recorded on a Perkin-Elmer Model 2000 FT-IR.

Example 1: Flow Preparation of (2R,5R)-((1R,2S,5R)-2-isopropyl-5-methylcyclohexyl) 5-hydroxy-1,3-oxathiolane-2-carboxylate (Formula Ia)

Formula Ia

L-Menthyl glyoxalate monohydrate (1.0 g, 4.34 mmol) in acetone (10 mL), was added to 1,4-dithiane 2,5-diol (396 mg, 2.60 mmol) and a catalytic amount of acetic acid (0.5 mL). The solutions were pumped at a flow rate 0.05 mL/min (for a combined flow rate of 0.1 mL/min, and the reaction solution was passed through a flow reactor at 125° C., and exited the flow system through a back pressure regulator (10 bar) to control the temperature and pressure. The reaction mixture was collected into a collection vial equipped with a septum. After completion of the reaction, as monitored by thin layer chromatography ("TLC") and gas chromatography ("GC"), the solvent was evaporated. The reaction mixture was cooled to 0° C.-5° C. and a 1% triethylamine in heptane or hexane solution was added drop wise. The mixture was stirred at 0° C. for 2-3 hours, observing the formation of precipitation. The isolated solid was filtered and washed with n-hexane to give (2R,5R)-((1R,2S,5R)-2-isopropyl-5-methylcyclohexyl) 5-hydroxy-1, 3-oxathiolane-2-carboxylate (1.1 g, 88%) as a white solid.

Spectral Analysis:
1H-NMR in CDCl$_3$ (400 MHz): ∂ 5.96 (d, 1H), 5.57 (d, 1H), 4.74 (s, 1H), 3.32-3.29 (m, 1H), 3.17-3.08 (dd, 1H), 2.02 (d, 2H), 1.70 (d, 1H), 1.51-1.42 (m, 2H), 1.09-1.00 (m, 2H), 0.91 (d, 6H), 0.78 (d, 3H). 13C-NMR in CDCl$_3$ (100 MHz): ∂ 16.27, 20.69, 23.30, 26.16, 31.42, 34.11, 38.46, 40.35, 46.86, 46.07, 80.20, 101.22, 103.20, 172.18. FT-IR (Neat): 3456, 2956, 2864, 1731, 1457, 1387, 1288, 1196, 1041, 986.
Nature of the compound: white solid
Flow rate: 0.1 mL/min
Residence Time: 20 min
Reaction temperature: 50° C. to 125° C.
Recrystallization: 1% in TEA in heptane/hexane
Confirmed by: GC, IR and $^1$H-NMR spectra Example 1A: Solvent Free Batch Preparation of (2R,5R)-((1R,2S,5R)-2-isopropyl-5-methylcyclohexyl) 5-hydroxy-1,3-oxathiolane-2-carboxylate (Formula Ia)

Formula Ia

L(-) Menthyl glyoxalate (25 g, 108.69 mmol) and 1,4-dithiane 2,5-diol (8.2 g, 54.32 mmol) were mixed together in a 250 mL round bottom flask for 30 minutes. The round bottom flask was charged with N$_2$, set up with a dean stark condenser and connected with a water circulator. Initially the reaction mixture melts at 80° C.-85° C. from solid to a thick brown liquid. Heating was then raised to 110° C. for 2-3 hours. After completion of the reaction, as monitored by GC and TLC, the reaction mixture was cooled to 0-5° C. A 1% solution of triethylamine in heptane (150 mL) was added slowly and allowed to stir and crystallise. The suspension was stirred at 0-5° C. for 2 hours. The product was isolated by filtration, washed with heptane and dried under the vacuum to give (2R,5R)-((1R,2S,5R)-2-isopropyl-5-methylcyclohexyl) 5-hydroxy-1,3-oxathiolane-2-carboxylate (26.5 g, 85.4%) as a white solid.

In a flow configuration, L(-) Menthyl glyoxalate would be added to a flask heated to 80° C.-85° C., at which point the glyoxylate melts; the viscous solution would then be pumped into a reactor using thermally controlled tubing in order to prevent precipitation in the lines. This would then be reacted with 1,4-dithiane 2,5-diol from the other inlet of the reactor. The workup of the reaction would be the same as above.

Spectral Analysis:

1H-NMR in CDCl3 (400 MHz): ∂ 5.96 (d, 1H), 5.57 (d, 1H), 4.74 (s, 1H), 3.32-3.29 (m, 1H), 3.17-3.08 (dd, 1H), 2.02 (d, 2H), 1.70 (d, 1H), 1.51-1.42 (m, 2H), 1.09-1.00 (m, 2H), 0.91 (d, 6H), 0.78 (d, 3H). 13C-NMR in CDCl3 (100 MHz): ∂ 16.27, 20.69, 23.30, 26.16, 31.42, 34.11, 38.46, 40.35, 46.86, 46.07, 80.20, 101.22, 103.20, 172.18. FT-IR (Neat): 3456, 2956, 2864, 1731, 1457, 1387, 1288, 1196, 1041, 986.

Example 2: Flow Preparation of (2R,5R)-((1R,2S, 5R)-2-isopropyl-5-methylcyclohexyl) 5-acetoxy-1,3-oxathiolane-2-carboxylate (Formula Ib)

Formula Ib

A sample loop A (50 mL) was filled with a solution of (2R,5R)-((1R,2S,5R)-2-isopropyl-5-methylcyclohexyl) 5-hydroxy-1,3-oxathiolane-2-carboxylate (10.0 g, 34.7 mmol)) dissolved in dichloromethane ("DCM"), and a sample loop B (50 mL) was filled with a stock solution of acetic anhydride (16.3 mL, 173.6 mmol) and pyridine (8.3 mL, 104.1 mmol) in DCM at room temperature. The two sample loops (A & B) were simultaneously switched into line and the starting solutions were pumped through a Uniqsis™ system at a flow rate of 0.1 mL/min each. The starting solutions were mixed in a T-mixing piece and the reaction solution (combined flow rate 0.2 mL/min.) passed through a PFA-coated stainless-steel reactor coil (10 mL) at room temperature. The output stream was collected in closed cap vial (250 mL). After the reaction completion was confirmed by TLC & GC, the mixture was quenched with ice water (100 mL), settled and the separated organic layers were washed with dilute HCl (50 mL), dried over anhydrous Na2SO4 and concentrated under the reduced pressure. 7.8 g of the acetyl compound was obtained as a brown coloured solid, with a mixture of diastereomers.

A sample of 780 mg was dissolved in 0.1 mL in TEA in 10 mL of hexane at −10° C. for 24 h, which yielded the desired product (2R,5R)-((1R,2S,5R)-2-isopropyl-5-methylcyclohexyl) 5-acetoxy-1,3-oxathiolane-2-carboxylate (550 mg, 48.24%).

Spectral Analysis:

1H-NMR in COM: ∂ 6.79 (d, 1H), 5.63 (s, 1H), 4.74 (d, 1H), 3.45 (dd, 1H), 3.16 (d, 1H), 2.11 (s, 3H), 2.03-1.95 (m, 2H), 1.70 (d, 2H), 1.41-1.33 (m, 2H), 1.08-1.02 (m, 2H), 0.99-0.91 (m, 6H), 0.76 (d, 3H). 13C-NMR in CDCl3 (100 MHz): ∂ 16.16, 20.71, 21.50, 23.24, 26.15, 31.37, 34.13, 37.33, 40.40, 47.07, 76.10, 79.90, 80.35, 99.65, 168.58, 169.64. FT-IR (Neat): 3463, 2959, 2932, 2865, 1745, 1730, 1463, 1385, 1287, 1169, 1040, 986, 876.

Nature of the compound: white solid

Flow rate: 0.2 mL/min

Residence Time: 50 min

Reaction temperature: room temperature

Confirmed by: GC, IR and ¹H-NMR spectra

Example 2A: Batch Preparation of (2R,5R)-((1R, 2S,5R)-2-isopropyl-5-methylcyclohexyl) 5-acetoxy-1,3-oxathiolane-2-carboxylate (Formula Ib)

Formula Ib

To a 500 mL two neck round bottom flask, charged with nitrogen, was added a stirred solution of (2R,5R)-((1R,2S, 5R)-2-isopropyl-5-methylcyclohexyl) 5-hydroxy-1,3-oxathiolane-2-carboxylate (25 g, 86.80 mmol) in acetonitrile (200 mL) at room temperature. Sodium bicarbonate (14.5 g, 173.11 mmol) and acetic anhydride (16.34 mL, 173.11 mmol) was added slowly and the reaction mixture was stirred for 6 hours at room temperature. The progress of the reaction monitored by TLC (using 20% EA+PE R$_f$~0.65) and GC. The reaction mixture was filtered, washed with acetonitrile and evaporated using rotary evaporation, then diluted with water (100 mL) and extracted with ethyl acetate (3×100 mL). The combined organic layers were dried over anhydrous Na2SO4 and concentrated under reduced pressure to give a mixture of four diastereomers. A sample of 5 g was dissolved in 80 mL of hexane with 1 mL of TEA, and after 36 hours at −20° C. the desired trans-(2R,5R) stereoisomer (2.4 g, 41.8%) was precipitated.

Spectral Analysis:

1H-NMR in CDCl3: ∂ 6.79 (d, 1H), 5.63 (s, 1H), 4.74 (d, 1H), 3.45 (dd, 1H), 3.16 (d, 1H), 2.11 (s, 3H), 2.03-1.95 (m, 2H), 1.70 (d, 2H), 1.41-1.33 (m, 2H), 1.08-1.02 (m, 2H), 0.99-0.91 (m, 6H), 0.76 (d, 3H). 13C-NMR in CDCl3 (100 MHz): ∂ 16.16, 20.71, 21.50, 23.24, 26.15, 31.37, 34.13, 37.33, 40.40, 47.07, 76.10, 79.90, 80.35, 99.65, 168.58, 169.64. FT-IR (Neat): 3463, 2959, 2932, 2865, 1745, 1730, 1463, 1385, 1287, 1169, 1040, 986, 876.

Example 3: Continuous Flow Protocol for First Two Steps (Uniqsis™) in the Preparation of (2R,5R)-((1R,2S,5R)-2-isopropyl-5-methylcyclohexyl) 5-acetoxy-1,3-oxathiolane-2-carboxylate (Formula Ib)

The first two steps of the process were conducted on a Uniqsis Flowsyn™ system according to the process detailed below.

Formula Ia

Formula Ib

TABLE 1

| Reagents used in the continuous flow synthesis process for producing the intermediate compound of the Formula Ib. | | | | |
|---|---|---|---|---|
| Reagents | Mwt | Mm | eq | Qty |
| L(−) menthyl glyoxalate | 230 | 4.34 | 1 | 1.0 g |
| 1,4-dithiane 2,5-diol | 152 | 2.60 | 0.6 | 396 mg |
| AcOH | — | — | 1 vol | 1 mL |
| Pyridine | 79 | 13.02 | 3 | 1.02 mL |
| Acetic anhydride | 102 | 21.70 | 5 | 2.21 mL |
| Acetone:DCM | | | 1:1 | 10 + 10 mL |

A stock solution of L(−) menthyl glyoxalate monohydrate (1 g, 4.34 mmol), 1,4-dithiane 2,5-diol (392 mg, 2.60 mmol) and acetic acid (1 mL) in acetone (10 mL) was heated to 50° C., until a clear solution was formed. This clear stock solution was pumped at a flow rate 0.1 mL/min through a 2 mL flow reactor at 125° C. The outlet of the flow reactor was connected to a back pressure regulator (10 bar) and the output stream was combined in a T-mixing piece (a cooling bath was arranged before the T-mixing piece to cool the first step solution). In another flask pyridine (1.02 mL, 13.02 mmol) and acetic anhydride (2.21 mL, 21.70 mmol) dissolved in DCM (10 mL) was pumped at a flow rate 0.1 mL/min and mixed at the T-mixing piece. The reaction flow rate from pump A (0.1 mL/min) and pump B (0.1 mL/min) combined for a total flow rate of 0.2 mL/min. The reaction mixture was passed through a PFA-coated stainless-steel reactor coil (10 mL) at room temperature. The output stream was collected in a closed cap vial (25 mL). After the reaction completion was confirmed by TLC and GC, the mixture was quenched with ice water (10 mL), settled and the separated organic layers were washed with dilute HCl (10 mL), dried over anhydrous $Na_2SO_4$ and concentrated under the reduced pressure. 700 mg of the acetyl compound was obtained as a brown coloured solid, with mixture of diastereomers. A sample of 700 mg was dissolved in 0.1 mL in TEA in 10 mL of hexane at −10° C. for 24 h which yielded the desired product (2R,5R)-((1R,2S,5R)-2-isopropyl-5-methylcyclohexyl) 5-acetoxy-1,3-oxathiolane-2-carboxylate (450 mg, 31.4% overall yield for two steps).

Spectral Analysis:

1H-NMR in CDCl3: ∂ 6.79 (d, 1H), 5.63 (s, 1H), 4.74 (d, 1H), 3.45 (dd, 1H), 3.16 (d, 1H), 2.11 (s, 3H), 2.03-1.95 (m, 2H), 1.70 (d, 2H), 1.41-1.33 (m, 2H), 1.08-1.02 (m, 2H), 0.99-0.91 (m, 6H), 0.76 (d, 3H). 13C-NMR in CDCl3 (100 MHz): ∂ 16.16, 20.71, 21.50, 23.24, 26.15, 31.37, 34.13, 37.33, 40.40, 47.07, 76.10, 79.90, 80.35, 99.65, 168.58, 169.64. FT-IR (Neat): 3463, 2959, 2932, 2865, 1745, 1730, 1463, 1385, 1287, 1169, 1040, 986, 876.

Nature of the compound: white solid

Flow rate: 0.2 mL/min

Reaction temperature: room temperature

Confirmed by: GC, IR and $^1$H-NMR spectra

Example 4: Flow Process Glycosylation Reaction of the Compound of Formula Ib in the Preparation of the Compound of Formula Id The compound of Formula Id may be prepared from the compound of Formula Ib according to the following flow process:

Formula II
wherein R = H or F

Formula Id

A solution of cytosine or fluoro cytosine (2.3 g, 20.72 mmol) and Bis(trimethylsilyl)acetamide (11.65 mL, 47.65 mmol) in acetonitrile (5 mL) were mixed under the nitrogen atmosphere at room temperature and heated to 80° C. in a 25 mL round bottom flask. A clear solution was obtained after 1 hour, indicating the formation of the of the silyl product. This product was diluted to 25 mL in an oven dried screw-cap volumetric flask.

A solution of (2R,5R)-((1R,2S,5R)-2-isopropyl-5-methylcyclohexyl) 5-acetoxy-1,3-oxathiolane-2-carboxylate (5.0 g, 19.60 mmol) and Trimethylsilyl iodide (2.7 mL, 19.60 mmol) in acetonitrile (25 mL) were prepared in separate oven dried, screw-cap volumetric flasks. The two solutions were then transferred into 10 mL stainless steel syringes (nucleobase was placed in the syringe wrapped around with heating tape and maintained at 60-65° C. during the reaction to prevent solid precipitation in the syringe). The reagent streams were pumped through a PFT tube at identical flow rates (each pump 0.1 mL/min; total flow rate: 0.2 mL/min) and kept at 100° C. using an oil bath. The reaction mixture was collected in a vial equipped with a septum. The collected solution was evaporated under the rotary pressure. The residue was purified by column chromatography using 60-120 silica mesh. The eluents were 4-5% Methanol in DCM. The pure products were recrystallized in Hexane: Ethyl acetate: Methanol (2:2:1) under reflux to get the clear white solids.

In another flow experiment, a similar reaction was performed in which the Trimethylsilyl iodide (TMSI) was replaced with Pyridium triflate. Both reactions gave the product in equal yield.

Spectral Analysis:

Analytical Data for (1R,2S,5R)-2-isopropyl-5-methylcyclohexyl(2R,5S)-5-(4-amino-2-oxo-1,2-dihydro-1-pyrimidinyl)-1,3-oxathiolane-2-carboxylate 1H-NMR in DMSO-d6 (400 MHz): ∂ 7.95 (d, 1H), 7.30-7.25 (d, 2H), 6.35 (t, 1H), 5.80-5.68 (m, 2H), 4.69 (q, 1H), 3.53 (d, 1H), 3.14-3.10 (m, 1H), 1.92-1.86 (m, 2H), 1.65 (d, 2H), 1.47-1.41 (m, 2H), 1.08-1.00 (m, 2H), 0.90-0.86 (m, 6H), 0.73 (d, 3H). 13C-NMR in CDCl3 (100 MHz): 169.45, 166.14, 140.92, 94.81, 89.28, 77.81, 77.77, 46.75, 40.63, 35.76, 33.97, 31.27, 26.15, 23.28, 22.25, 20.95 and 16.57.

Analytical Data for (1R,2S,5R)-2-isopropyl-5-methylcyclohexyl (2R,5S)-5-(4-amino-5-fluoro-2-oxo-1,2-dihydro-1-pyrimidinyl)-1,3-oxathialane-2-carboxylate 1H-NMR in CDCl3 (400 MHz): ∂ 8.43 (d, 1H), 7.42 (bs, 1H), 6.35 (d, 1H), 5.71 (bs, 2H), 5.39 (s, 1H), 4.73 (t, 1H), 3.48 (dd, 1H), 3.07 (dd, 1H), 1.97-1.85 (m, 2H), 1.64 (d, 2H), 1.44-1.35 (m, 2H), 1.05 (t, 2H), 0.97-0.83 (m, 6H), 0.78 (d, 3H). 13C-NMR in CDCl3 (100 MHz): 169.77, 158.11, 153.38, 134.71, 125.50 89.59, 78.31, 75.58, 46.86, 40.63, 36.74, 34.02, 31.25, 26.21, 23.38, 22.25, 20.88 and 16.58.

Nature of the compound: white solids
Flow rate: 0.2 mL/min
Residence Time: 9.3 min
Reaction temperature: room temperature to 120° C.
Confirmed by: GC, IR and ¹H-NMR spectra Example 4A: Batch Glycosylation Reaction of the Compound of Formula Ib in the Preparation of the Compound of Formula Id The compound of Formula Id may be prepared from the compound of Formula Ib according to the following batch process:

To a solution of nucleobase (1.0 eq) in acetonitrile (5 mL) was added slowly Bis(trimethylsilyl)acetamide (2.5 eq) under nitrogen atmosphere at room temperature. The reaction mixture was heated to 80° C. for 1 hour when the reaction mixture formed a clear solution, indicating the formation of the silyl product. The reaction mixture was cooled to ambient temperature and used in the next step without any further isolation.

A solution of (2R,5R)-((1R,2S,5R)-2-isopropyl-5-methylcyclohexyl) 5-acetoxy-1,3-oxathiolane-2-carboxylate (1.0 eq) in acetonitrile (10 mL) was added to the above mixture, and stirred for 10 minutes. Iodotrimethylsilane (1.0 eq) was introduced drop wise via a cannula at room temperature. The reaction mixture was heated to 80° C. for 2 hours with the progress of the reaction monitored by TLC and GC. After completion of the reaction the reaction mixture was quenched with the addition of an aqueous solution of Na$_2$S$_2$O$_3$ (15 mL). The solvent was removed by rotary evaporation and extracted with ethyl acetate (3×50 mL). The combined organic layers were washed with water (25 mL), brine (25 mL) solution, and a saturated solution of NaHCO₃ (25 mL). The organic layer was dried under the anhydrous Na₂SO₄ and concentrated by using rotary pressure to get the crude residue. The crude compound was purified by column chromatography using 100-200 silica mesh and MeOH: DCM (6:94) as a diluent. The ¹H-NMR spectrum of this material indicated that it was a mixture of the cis- and trans-diastereomers. The solid product was recrystallised using a mixture of ethyl acetate, hexane, and methanol to produce the required isomer.

Spectral Analysis:

Analytical Data for (1R,2S,5R)-2-isopropyl-5-methylcyclohexyl(2R,5S)-5-(4-amino-2-oxo-1,2-dihydro-1-pyrimidinyl)-1,3-oxathialane-2-carboxylate 1H-NMR in DMSO-d6 (400 MHz): ∂ 7.95 (d, 1H), 7.30-7.25 (d, 2H), 6.35 (t, 1H), 5.80-5.68 (m, 2H), 4.69 (q, 1H), 3.53 (d, 1H), 3.14-3.10 (m, 1H), 1.92-1.86 (m, 2H), 1.65 (d, 2H), 1.47-1.41 (m, 2H), 1.08-1.00 (m, 2H), 0.90-0.86 (m, 6H), 0.73 (d, 3H). 13C-NMR in CDCl3 (100 MHz): 169.45, 166.14, 140.92, 94.81, 89.28, 77.81, 77.77, 46.75, 40.63, 35.76, 33.97, 31.27, 26.15, 23.28, 22.25, 20.95 and 16.57.

Analytical Data for (1R,2S,5R)-2-isopropyl-5-methylcyclohexyl (2R,5S)-5-(4-amino-5-fluoro-2-oxo-1,2-dihydro-1-pyrimidinyl)-1,3-oxathialane-2-carboxylate 1H-NMR in CDCl3 (400 MHz): ∂ 8.43 (d, 1H), 7.42 (bs, 1H), 6.35 (d, 1H), 5.71 (bs, 2H), 5.39 (s, 1H), 4.73 (t, 1H), 3.48 (dd, 1H), 3.07 (dd, 1H), 1.97-1.85 (m, 2H), 1.64 (d, 2H), 1.44-1.35 (m, 2H), 1.05 (t, 2H), 0.97-0.83 (m, 6H), 0.78 (d, 3H). 13C-NMR in CDCl3 (100 MHz): 169.77, 158.11, 153.38, 134.71, 125.50 89.59, 78.31, 75.58, 46.86, 40.63, 36.74, 34.02, 31.25, 26.21, 23.38, 22.25, 20.88 and 16.58.

Example 5: Flow Process Reduction Reaction of the Compound of Formula Id

Formula Id

Formula I
R = H: Lamivudine
= F: Emtricitabine

A suspension of the compound of Formula Id (1 eq) in MeOH:H₂O (2:3 mL) was placed into oven dried 5 mL syringe. A prepared solution of potassium hydrogen phosphate (3 eq) in 3 mL water and sodium borohydride (2 eq) in 1.5 mL water+0.5 mL 25% w/w sodium hydroxide was placed into another oven dried syringe. Both syringes were fitted with individual Chemtrix™ flow pumps. The pumps were connected to a T-joint, with the product stream leading to pumped into micro reactor (individual flow rate 0.1 mL/min, total flow rate 0.2 mL/min).

The collected solution was quenched with dilute solution of HCl (pH 4-4.5), extracted with diethyl ether to remove the methanol, then pH adjusted to 7 using a saturated NaHCO₃ solution. The solution was filtered through a centred funnel and evaporated by rotary evaporation. The crude product was purified by column chromatography using 60-120 silica mesh with a diluent mixture of Hexane:Ethyl acetate:MeOH (1:1:1) to obtain the pure product.

Example 5A: Batch Process Reduction Reaction of the Compound of Formula Id

Formula Id

Formula I
R = H: Lamivudine
= F: Emtricitabine

A suspension of nucleoside (1 eq) in methanol and water (2:1) was added to a solution of K$_2$HPO$_4$ (3 eq) in water (2 mL) at room temperature. After 15 minutes of stirring a solution of NaBH$_4$ (2 eq) in water (2 mL) containing 25% w/w NaOH solution was added to the reaction mixture. The reaction mixture was stirred for 2 hours at room temperature, with the progress of the reaction monitored by TLC. The reaction was quenched with HCl, pH adjusted to 4-4.5, and washed with diethyl ether to remove any unreacted starting material and menthol. The aqueous layer was pH adjusted to 7-7.2 using a 2M NaOH solution, the mixture was filtered through a celite pad, and concentrated under reduced pressure rotary evaporation. The crude compound was purified by column chromatography and recrystallised using Ethyl acetate:MeOH to give the pure compounds.

Spectral Analysis:

Analytical data for 4-amino-1-((2R,5S)-2-(hydroxymethyl)-1,3-oxathiolan-5-yl)pyrimidin-2(1H)-one (Lamivudine)

1H-NMR in CD3OD-d4 (400 MHz): ∂ 8.06 (d, J=7.52, 1H), 6.30 (t, J=4.72, 1H), 5.90 (d, J=7.52, 1H), 5.29 (t, J=3.72, 1H), 3.94 (dd, J=3.48, 2H), 3.88 (dd, J=4.28, 1H), 3.53 (dd, J=5.4, 12.0, 1H), 3.14 (dd, J=4.36, 11.96, 1H). 13C-NMR in CD3OD-d4 (100 MHz): 166.35, 156.53, 141.33, 94.30, 87.45, 86.56, 62.67, 37.05. Anal. calcd for C8H11N3O3S: C, 41.91, H, 4.84, N, 18.33, S, 13.99. Found: C, 41.88, H, 4.71, N, 18.19 S, 13.91.

Analytical Data for 4-amino-5-fluoro-1-((2R,5S)-2-(hydroxymethyl)-1,3-oxathiolan-5-yl)pyrimidin-2(1H)-one (Emtricitabine)

1H-NMR in CD3OD-d4 (400 MHz): ∂ 8.36 (d, J=6.92, 1H), 6.25 (ddd, J=1.64, 5.2, 7.03, 1H), 5.30 (t, J=3.36, 1H), 4.02 (dd, J=3.03, 12.6, 2H), 3.88 (dd, J=3.56, 12.6, 1H), 3.54 (dd, J=5.36, 12.16, 1H), 3.19 (dd, J=3.63, 12.12, 1H). 13C-NMR in CD3OD-d4 (100 MHz): 158.31 (d, J=14), 154.83, 136.24 (d, J=240.2), 125.8 (d, J=33.3), 87.45, 87.34, 62.02, 37.50.

This above description of some of the illustrative embodiments of the invention is to indicate how the invention can be made and carried out. Those of ordinary skill in the art will know that various details may be modified thereby arriving at further embodiments, but that many of these embodiments will remain within the scope of the invention.

The invention claimed is:

1. A flow synthesis process for producing a compound of the Formula I and its pharmaceutically acceptable salts, Formula I the process comprising the steps of:

a) reacting L-menthyl glyoxalate with 1,4-dithiane-2,5-diol in a dehydration reaction to form a reaction product comprising a compound of the Formula Ia

Formula Ia b) reacting the reaction product of step (a) with an acetylation reagent to form a reaction product comprising a compound of the Formula Ib

Formula Ib c) reacting the reaction product of step (b) with pyridine triflate and a compound of the Formula Ic Formula Ic in a glycosylation reaction to form a reaction product comprising a compound of the Formula Id Formula Id and d) reacting the reaction product of step (c) with a reducing agent to form the compound of Formula I,
wherein R is selected from H or F, and
wherein steps (a) to (b) and (c) to (d) are continuous flow synthesis steps, such that the compound of Formula Ib is the only intermediate isolated in the process.

2. The process according to claim 1, wherein steps (a) to (d) are continuous flow synthesis steps, such that no isolated intermediates are produced in the process.

3. The process according to claim 1, wherein prior to step (a) the L-Menthyl glyoxalate is produced from a reaction of L(−) Menthol with glyoxalic acid in cyclohexane, wherein the L(−) Menthol is recovered as a by-product from the reaction mixture formed in step (d).

4. The process according to claim 1, wherein the compound of Formula Ic

Formula Ic used in step (c) is produced by reacting a compound of Formula II

Formula II with Bis(trimethylsilyl)acetamide in the presence of an organic solvent.

5. The process according to claim 4, wherein the organic solvent is acetonitrile.

6. The process according to claim 1, wherein in step (b) the acetylation reagent is a mixture of acetic anhydride and pyridine, or acetic anhydride and sodium carbonate.

7. The process according to claim 1, wherein the reaction of step (a) is a solvent free reaction.

8. The process according to claim 1, wherein in step (a) the reaction of L(−) Menthyl glyoxalate and 1,4-dithiane 2,5-diol is conducted in an organic solvent.

9. The process according to claim 1, wherein in step (b) the reaction of the acetylation reagent, with the compound of Formula Ia Formula Ia is conducted in the presence of an organic solvent.

10. The process according to claim 8, wherein the organic solvent is acetone.

11. The process according to claim 1, wherein the organic solvent in step (c) is acetonitrile.

12. The process according to claim 9, wherein the organic solvent is acetone.

* * * * *